US00PP25502P3

(12) United States Plant Patent
Sills et al.

(10) Patent No.: US PP25,502 P3
(45) Date of Patent: May 5, 2015

(54) BLACKBERRY PLANT NAMED 'DRISBLACKSIX'

(50) Latin Name: ***Rubus* L. subgenus *Rubus***
Varietal Denomination: DrisBlackSix

(71) Applicant: Driscoll Strawberry Associates, Inc., Watsonville, CA (US)

(72) Inventors: Gavin R. Sills, Gilroy, CA (US); Andrea M. Pabon, Gilroy, CA (US); Stephen B. Moyles, Soquel, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 154 days.

(21) Appl. No.: 13/986,857

(22) Filed: Jun. 12, 2013

(65) Prior Publication Data

US 2014/0373227 P1 Dec. 18, 2014

(51) Int. Cl.
*A01H 5/00* (2006.01)

(52) U.S. Cl.
USPC ..... Plt./203

(58) Field of Classification Search
USPC ..... Plt./203
See application file for complete search history.

*Primary Examiner* — Annette Para
(74) *Attorney, Agent, or Firm* — Jondle & Associates, P.C.

(57) ABSTRACT

This invention relates to a new and distinct variety of blackberry plant named 'DrisBlackSix', particularly characterized by high yields, long production season and vigorous plants, is disclosed.

2 Drawing Sheets

Genus and species: *Rubus* L. subgenus *Rubus*.
Variety denomination: 'DrisBlackSix'.

BACKGROUND OF THE NEW PLANT

The present invention relates to a new and distinct blackberry cultivar designated 'DrisBlackSix' and botanically known as *Rubus* L. subgenus *Rubus*. This new blackberry variety was identified in Santa Cruz County, Calif. in June 2005 and originated from a cross between the female parent blackberry plant 'BF785-1' (unpatented) and the male parent blackberry plant 'Driscoll Cowles' (U.S. Plant Pat. No. 14,780). The original seedling of the new cultivar was first asexually propagated by tissue culture and root cuttings at a nursery in Santa Cruz County, Calif. in 2005. 'DrisBlackSix' was subsequently asexually propagated by tissue culture and root cuttings and underwent further testing at a nursery in Santa Cruz County, Calif. from 2010 to 2012. The present invention has been found to be stable and reproduce true to type through successive asexual propagations.

Plant Breeder's Rights for this variety have not been applied for. 'DrisBlackSix' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz County, Calif.

1. High yields;
2. Long production season; and
3. Vigorous plants.

DESCRIPTION OF THE PHOTOGRAPHS

This new blackberry plant is illustrated by the accompanying photographs which show the plant's canes, fruit, and leaves. The colors shown are as true as can be reasonably obtained by conventional photographic procedures. The photographs are of plants that are 4 years old.

Figure 1:
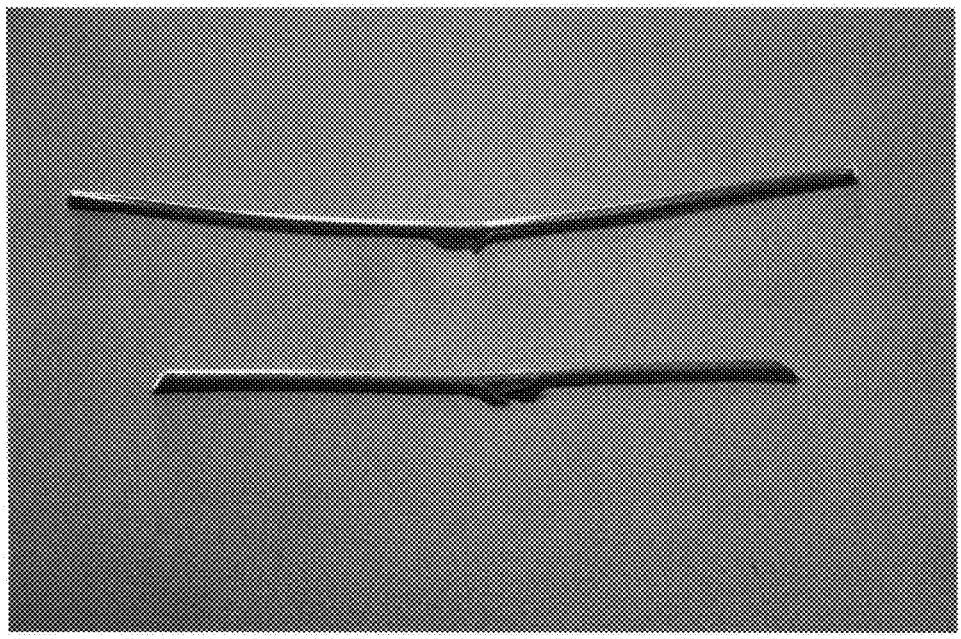
Figure 2:
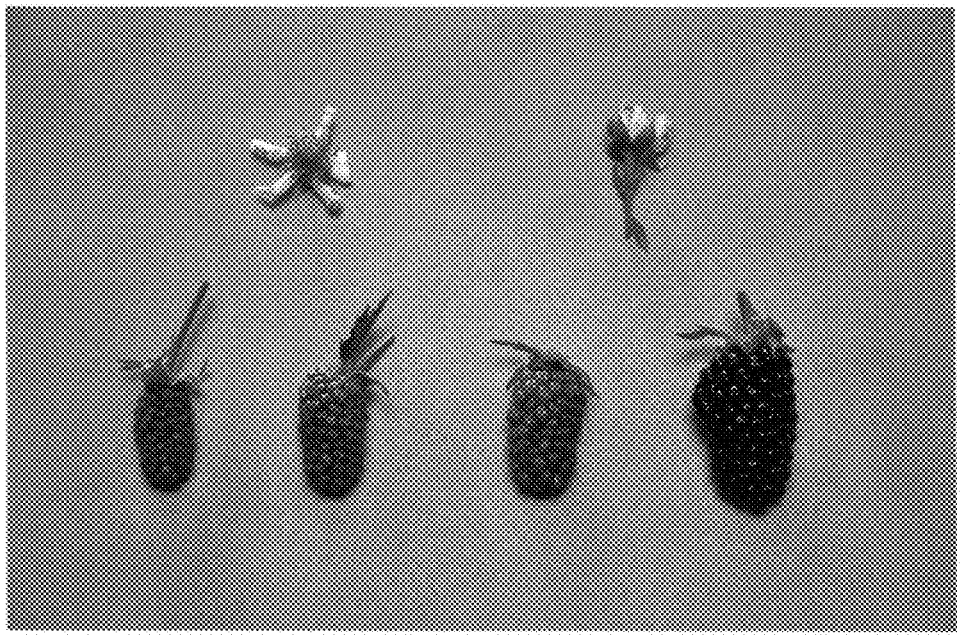
Figure 3:
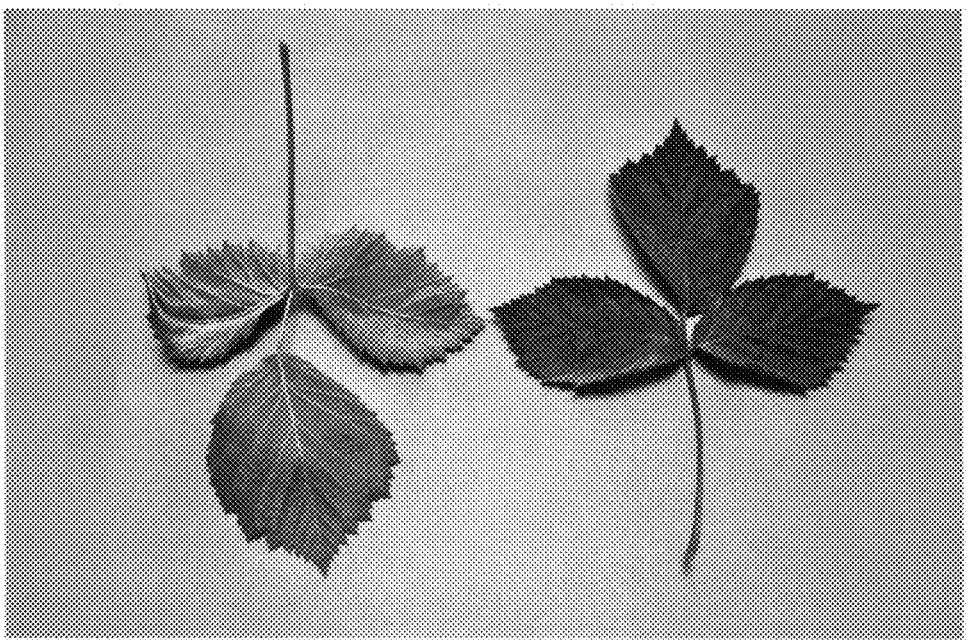

FIG. 1 shows a section of a young cane without spines.
FIG. 2 shows the flowers and the fruit at various stages.
FIG. 3 shows the upper and lower surfaces of the leaves.

DESCRIPTION OF THE NEW VARIETY

The following descriptions of 'DrisBlackSix' are based on observations made in Santa Cruz County, Calif. on 4-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackSix' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* $2^{nd}$ edition, by James G. Harris and Melinda Woolf Harris, unless where otherwise defined.

DETAILED BOTANICAL DESCRIPTION

Classification:
- *Family*.—Rosaceae.
- *Botanical*.—*Rubus* L. subgenus *Rubus*.
- *Common name*.—Blackberry.
- *Variety name*.—'DrisBlackSix'.

Parentage:
- *Female parent*.—Proprietary blackberry plant named 'BF785-1' (unpatented).
- *Male parent*.—Proprietary blackberry plant named 'Driscoll Cowles' (U.S. Plant Pat. No. 14,780).

Plant:

*Vigor*.—High.

*Growth habit*.—Semi-upright.

*Productivity*.—High.

*Propagation*.—Tissue culture and root cuttings.

*Self-fruitfulness*.—Self-fruitful.

*Time of bud burst*.—Early to medium.

Canes:

*Fruiting lateral length* ($4^{th}$ *lateral from tip*).—Average: Medium to long; 58.5 cm.

*Number of fruit per lateral*.—Average: 11.0.

*Fruiting on current year's cane*.—Absent.

*Cane internodal distance*.—Average: 8.7 cm.

*Number of new canes during flowering*.—Few.

*New cane strength* (*observed full-grown shoot after picking*).—Strong.

*Glaucosity observed on full-grown shoot after picking*.—Medium.

*Spines*.—Absent.

*Young shoots*.—Quantity: Few. Time of emergence from soil: Medium. Anthocyanin coloration (during rapid growth): Strong; RHS 183A (Dark greyed-purple). Intensity of green color: Medium; RHS 144A (Medium yellow-green). Number of glandular hairs: Medium on laterals; absent or few on main cane.

*Dormant cane*.—Length: Long. Diameter (in central third): Medium. Cross section (from mid cane observed at end of first growing season): Rounded to angular. Color: Sunny side: RHS 183A (Dark greyed-purple). Shade side: RHS 144A (Medium yellow-green). Number of branches: Medium. Distribution of branches: Over whole length. Anthocyanin coloration: Strong; RHS 183A (Dark greyed-purple). Spines: Absent.

Leaves:

*Type*.—Palmate.

*Predominant number of leaflets*.—Three to seven.

*Overlapping or relative position of lateral leaflets*.—Free.

*Color*.—Upper surface: Medium; RHS 143A (Medium green). Lower surface: Light; RHS 144A (Medium yellow-green).

*Glossiness of upper side*.—Medium.

*Cross section profile*.—Concave (margins rolled inwards).

*Leaflets*.—Shape: Oval to ovate. Margin: Serrate. Depth of incisions: Shallow. Type of incision margin: Biserrate. Apex: Truncate to acuminate. Base: Obtuse. Rachis length between terminal leaflet and adjacent lateral leaflet: Average: 24.5 mm.

*Lateral leaflet* (*basal pair*).—Length: Average: 86.3 mm. Width: Average: 60.3 mm. Length/width ratio: 1.4.

*Terminal leaflet*.—Length: Average: Short; 118.0 mm. Width: Average: Medium; 74.0 mm. Length/width ratio: 1.6. Lobing: Absent. Undulation of margin (rippling of margin): Weak to medium. Blistering between veins (rugosity): Weak. Shape: Oval to ovate. Tip: Truncate. Base: Obtuse. Margin: Crenate. Cross-section: U-shaped.

*Petiole*.—Length average: 17.5 mm. Diameter average: 1.2 mm. Pigmentation: Upper surface: Medium; RHS 137A (Dark green). Lower surface: Light; RHS 137D (Medium green).

*Stipule*.—Size: Medium. Orientation: Erect.

Inflorescence:

*Time of beginning of flowering on previous year's cane*.—Early.

*Time of beginning of flowering on current year's cane*.—N/A.

*Flower diameter*.—Average: Medium; 37.0 mm.

*Flower number* (*at* $3^{rd}$ *node from tip of lateral*).—Average: 1.

*Petal*.—Length: Average: 16.4 mm. Width: Average: 11.19 mm. Length/width ratio: 1.5. Color: RHS N155A (White) and RHS 68D (Medium red-purple).

*Pedicel*.—Length: Average: 40.8 mm. Diameter: Average: 1.22 mm.

Fruit:

*Time of ripening on previous year's cane*.—Medium.

*Time of ripening on current year's cane*.—N/A.

*Harvest interval*.—Early June to late July.

*Color*.—Immature: RHS 146A (Dark yellow-green). Maturing: RHS 183B (Dark greyed-purple). Mature: RHS 202A (Black).

*Glossiness*.—Medium.

*Shape in longitudinal section*.—Narrow ovate.

*Size*.—Medium.

*Length*.—Average: Medium to long; 28.78 mm.

*Width*.—Average: Medium; 19.44 mm.

*Ratio of length to width*.—1.5 (longer than broad).

*Weight* (*g/fruit*).—6.9 g.

*Soluble solids* (%) (*in Brix*).—10.2.

*Titratable acidity*.—(% as citric acid): 1.3.

*Seed weight* (*g/seed*).—0.284.

*Number of druplets/fruit*.—Many; 35.

*Size of druplet*.—Medium.

*Firmness*.—Medium to firm.

*Yield*.—Medium to high.

Disease, pest, and stress resistance: Not tested.

COMPARISON WITH PARENTAL AND COMMERCIAL VARIETIES

'DrisBlackSix' differs from the proprietary female parent 'BF785-1' (unpatented) in that 'DrisBlackSix' is thornless, whereas 'BF785-1' is thorny. Additionally, 'DrisBlackSix' has smaller fruit than 'BF785-1'.

'DrisBlackSix' differs from the proprietary male parent 'Driscoll Cowles' (U.S. Plant Pat. No. 14,780) in that 'DrisBlackSix' has earlier production than 'Driscoll Cowles'.

'DrisBlackSix' differs from the commercial variety 'Driscoll Carmel' (U.S. Plant Pat. No. 15,058) in that 'DrisBlackSix' has high vigor and few young shoots, whereas 'Driscoll Carmel' has moderate vigor and a medium number of young shoots. Additionally, 'DrisBlackSix' is thornless and has medium glossy fruit, whereas 'Driscoll Carmel' has spines and strongly glossy fruit.

We claim:

1. A new and distinct variety of blackberry plant named 'DrisBlackSix' as described and shown herein.

* * * * *